United States Patent
El-Ayari et al.

(10) Patent No.: US 11,147,711 B2
(45) Date of Patent: Oct. 19, 2021

(54) DEVICE FOR APPLYING A MARKING TO THE HUMAN EYE

(71) Applicant: GEUDER AG, Heidelberg (DE)

(72) Inventors: Hamadi El-Ayari, Frankfurt (DE); Julius Mueller-Albinus, Birkenau (DE); Hartmut Fath, Wiesloch (DE)

(73) Assignee: GEUDER AG, Heidelberg (DE)

( * ) Notice: Subject to any disclaimer, the term of this patent is extended or adjusted under 35 U.S.C. 154(b) by 352 days.

(21) Appl. No.: 15/756,742

(22) PCT Filed: Aug. 23, 2016

(86) PCT No.: PCT/DE2016/200391
§ 371 (c)(1),
(2) Date: Oct. 5, 2018

(87) PCT Pub. No.: WO2017/036475
PCT Pub. Date: Mar. 9, 2017

(65) Prior Publication Data
US 2019/0021909 A1    Jan. 24, 2019

(30) Foreign Application Priority Data
Sep. 1, 2015 (DE) .................. 10 2015 216 723.2

(51) Int. Cl.
*A61F 9/013* (2006.01)
*A61B 90/00* (2016.01)

(52) U.S. Cl.
CPC ............ *A61F 9/0136* (2013.01); *A61B 90/39* (2016.02); *A61B 2090/395* (2016.02); *A61B 2090/3908* (2016.02)

(58) Field of Classification Search
CPC ........ A61F 9/013; A61F 9/0136; A61F 9/007; A61B 90/39; A61B 2090/3908; A61B 2090/395
See application file for complete search history.

(56) References Cited

U.S. PATENT DOCUMENTS 4,440,168 A     4/1984 Warren
9,011,470 B2 *  4/2015 Mackool ............... A61F 9/0136
                                                    606/166

(Continued)

FOREIGN PATENT DOCUMENTS

CN        102596122 A       7/2012
DE    20 2008 004 593 U1    7/2008

(Continued)

OTHER PUBLICATIONS

International Search Report and Written Opinion for International Application No. PCT/DE2016/200391 (with English Translation of Search Report), dated Jan. 3, 2017, 14 pages.

(Continued)

*Primary Examiner* — Sarah A Simpson
(74) *Attorney, Agent, or Firm* — Seed IP Law Group LLP

(57) ABSTRACT

A device for applying a marking to the human eye, in particular to the cornea of the eye, comprises a marking head comprising a marking element and a holding device carrying the marking head or an intermediate adapter. The marking head or the intermediate adapter has a bearing area which is rotatably mounted in a bearing ring of the holding device which surrounds the bearing area in a predeterminable or variable angular position.

20 Claims, 18 Drawing Sheets

(56) References Cited

U.S. PATENT DOCUMENTS

| | | | |
|---|---|---|---|
| 2006/0229495 A1* | 10/2006 | Frith | A61B 1/00126 |
| | | | 600/112 |
| 2009/0254108 A1 | 10/2009 | Davis | |
| 2011/0251630 A1* | 10/2011 | Richardson | A61F 9/0136 |
| | | | 606/166 |
| 2012/0209280 A1 | 8/2012 | Macken | |
| 2012/0245609 A1 | 9/2012 | Brown | |
| 2013/0035705 A1* | 2/2013 | Fath | A61F 9/0136 |
| | | | 606/166 |
| 2014/0324083 A1* | 10/2014 | Brown | A61F 9/0136 |
| | | | 606/166 |

FOREIGN PATENT DOCUMENTS

| | | |
|---|---|---|
| DE | 20 2010 012 367 U1 | 12/2010 |
| EP | 2 453 854 B1 | 3/2014 |

OTHER PUBLICATIONS

Chinese First Office Action for CN201680062069.4 dated Nov. 21, 2019, 12 pages.

\* cited by examiner

DEVICE FOR APPLYING A MARKING TO THE HUMAN EYE

BACKGROUND

Technical Field

The present application relates to a device for applying a marking to the human eye, in particular to the cornea of the eye.

Description of the Related Art

There is a fundamental need for marking the cornea of the human eye, namely in the preparation for ophthalmological interventions in the case of a correction of astigmatism, preferably for producing the close-fitting attachment of a lens to the iris.

Generic devices are already known from practice, usually under the name of "marking instrument."

Such a marking instrument, which is used for generating markers for ophthalmological surgery, is known from DE 20 2008 004 593 U1. The known instrument comprises a marking head which is pivotally connected to an instrument handle. A marking element provided on the instrument head is arranged adjustably in its angular position relative to a plumb weight so that markings with an angular setting relative to the vertical direction can be generated.

US 2009/0254108 A1 discloses a similar instrument, namely a device for applying a marking to the human eye, more precisely to the cornea. The instrument comprises a marking head and a holding device carrying the marking head, wherein the marking head has a marking element and a carrier which holds the marking element in a predeterminable or changeable angular position. The carrier is arranged rotationally fixed with respect to the holding device or a reference line. The marking head is connected to the holding device.

A generic device is known from EP 2 453 854 B1, wherein this device is based on the aforementioned US document as a starting point. In the generic device, the marking head has coupling means for directly or indirectly connecting to the holding device for inserting a connector. The connector is assigned to the holding device or to an intermediate adapter. Alternatively, the marking head may comprise a connector with an insertion area for direct coupling to the holding device, namely for direct insertion into a connector of the holding device, said connector being designed as a slotted sleeve.

The generic device is problematic as far as handling is concerned, more specifically with regard to "finding" the correct marking location. The device itself or the marking head blocks the view of the place on the eye that is to be marked.

In addition, the mounting of the marking head is inadequate in the known device. As a rule a plain bearing made of Teflon is used here, which is subject to considerable wear and, moreover, when dirty only inadequately performs its purpose of providing a perfect mounting while ensuring a low-friction rotatability of the marking head.

BRIEF SUMMARY

The present disclosure is therefore based on the task of designing and developing a device of the generic type such that it can be handled easily with good accuracy. The marking on the eye should be reproducible. In addition, a perfect and robust mounting for the marking head should be attained.

Accordingly, described herein is a device that, in various embodiments, comprises a marking head with a marking element and a holding device carrying the marking head or an intermediate adapter. The marking head or the adapter comprises a bearing area, that is rotatably mounted in a bearing ring of the holding device encompassing the bearing area in an angular position that can be predetermined or changed or set.

It is advantageous for the mounting of the marking head or an intermediate adapter for a special holding device to be provided. For this purpose, the marking head or the adapter has a bearing area which is rotatably mounted in a bearing ring of the holding device that surrounds the bearing area. The bearing ring of the holding device thus encloses the bearing area of the marking head or of the adapter, wherein it is advantageous if the marking head or the adapter can be removed or pulled out of the bearing ring in order to disassemble the device. The marking head with its marking element should be rotatably or pivotably insertable directly or indirectly into the bearing ring of the holding device and preferably freely rotatable therein. The bearing ring itself is assigned for handling a handle, an apparatus, a device or the like, wherein the marking head can rotate using gravity regardless of the orientation of the handle and so on. This will be discussed later.

Advantageously, a ball bearing is provided for mounting the marking head in the bearing ring of the holding device, said ball bearing acting between the bearing ring of the holding device and the bearing area of the marking head or of the adapter. The ball bearing can be made entirely of stainless steel. It is also conceivable for the cage of the ball bearing to be made of stainless steel and for the balls to be made of wear-resistant ceramic. Even the entire bearing can be made of ceramic.

In a further advantageous manner, the marking head and possibly the adapter has a preferably coaxial passage. This passage ends in the region of the marking element (distally) with a coaxial sighting tube or a centrally located sleeve, through which it is possible to "aim" from the rear side of the device through the device. The sighting tube preferably ends before the operating area of the marking element, so that the sighting tube at all times remains out of contact with the cornea of the eye, since it is set back.

The marking element may comprise two or four marking blades lying diametrically opposite to each other in pairs, wherein the provision of at least two blades is absolutely necessary. The provision of three marking blades, arranged in a star shape, is also conceivable. In the case of more than two blades being provided, a secure, tilt-free placement on the cornea of the eye is ensured Regardless of the number of marking blades, it is possible that these are each designed to mark a straight line or at least two points on or sections of a straight line. In concrete terms, the marking blade can be serrated, preferably at least partially curved to conform to the ocular surface.

With regard to the mounting and movement of the marking element or of the marking head, it is advantageous for the marking head to be rotatable in the bearing ring of the holding device by hand or by means of a tool (to be understood in the broadest sense), namely in a predeterminable angular position with respect to the horizontal or vertical direction.

It is also advantageous for a marking ring to be provided to show the angular position of the marking element or marking blades that has been set, said ring having a marking indicating the angular position of the holding device. Furthermore, a scale ring of the marking head is provided which comprises a scale for indicating the angular position by means of the marking ring or by its marking, preferably in the range of 0° to 180°.

It should be noted at this point that the marking element is non-rotatably connected to or within the marking head. The scale ring of the marking head, together with its scale, is non-rotatably connected to the marking element or the marking blades. The marking head is rotatably mounted in the bearing ring of the holding device. Furthermore, the marking ring of the holding device is arranged rotatably with respect to the bearing ring but non-rotatably connected to the marking head being used, so that its marking symbolizing the angular position corresponding to the set angular position of the marking head or of the scale ring points to a degree number and symbolizes the corresponding angular position. The entire arrangement can be rotated in the rotary ring, wherein the angular position of the marking head can be predetermined.

In the context of a further embodiment, it is conceivable that coupling means are provided between the marking head and the holding device or the adapter, which preferably comprise latching means for mutual latching to which spring force is applied. Any designs for a suitable coupling are conceivable.

In the case of the holding device, this may be a conventional ophthalmological device without its actual functional head. For example, a slit lamp can serve this purpose.

It has already been mentioned that the marking head can be connected directly or indirectly to the device, for example, to the slit lamp. In the case of indirect coupling, the marking head can be connected to the device via a coupling means or via an adapter comprising a connector.

A hand-held ophthalmological instrument, preferably with a gravity-loaded pendulum receptacle for the marking head that is aligned in the horizontal or vertical direction, may also serve as a holding device. In this regard refer, only by way of example, to EP 2 453 854 B1, which mentions a so-called pendulum marker.

With such a pendulum marker, the weight and the length of the pendulum orienting the marking head can be realized differently. A long pendulum oscillates for a longer time, while a short pendulum settles after only a few swings. Instead of a pendulum, pins or the like can also be provided. It is essential for the pendulum or the pin to provide a visual check, wherein the number of degrees of the angular position of the marking head is displayed on the aforementioned scale.

There are various options for advantageously designing and developing the teaching of the present disclosure. In this regard, reference is made, on the one hand, to the claims dependent upon claim 1 and, on the other hand, to the following explanation of two exemplary embodiments of the disclosure with reference to the drawings. Generally preferred designs and developments of the teaching are also explained in conjunction with the explanation of the preferred exemplary embodiments of the present disclosure with reference to the drawings.

DETAILED DESCRIPTION

Figure 1:
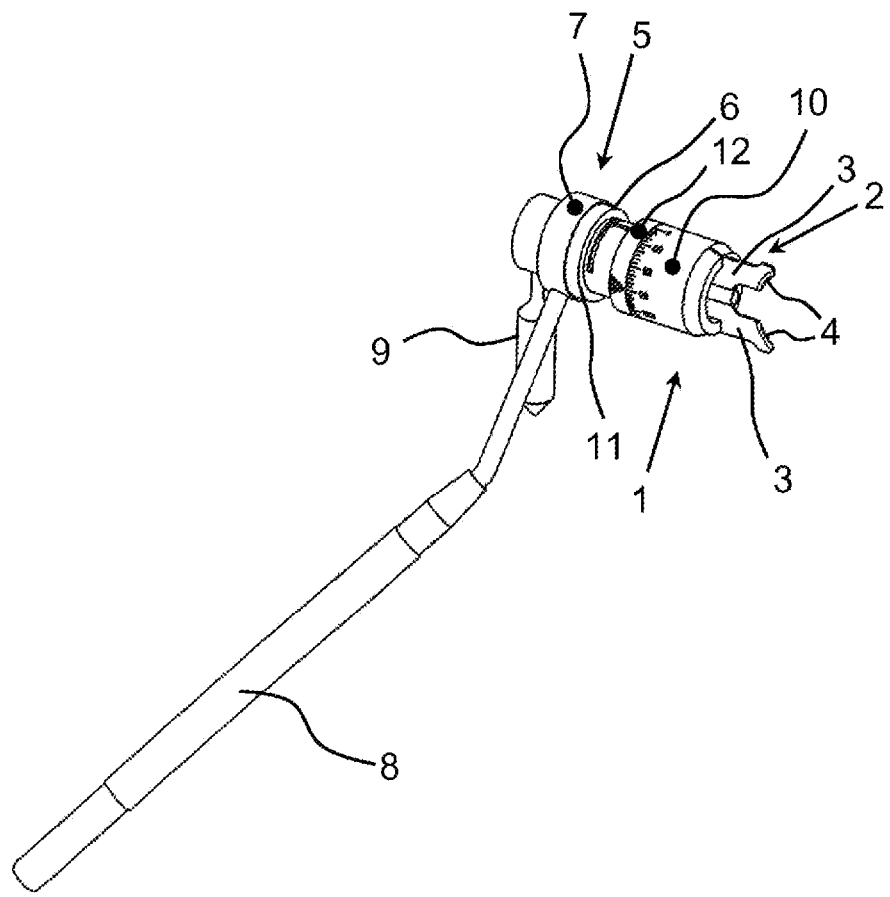
FIG. 1 shows a schematic view of a first exemplary embodiment of a device according to the present disclosure in the form of a so-called pendulum marker, comprising a marking head with a marking element having two marking blades.

FIG. 1 shows an exemplary embodiment of a device according to the present disclosure, which in this case is a so-called pendulum marker. The pendulum marker comprises a marking head 1, which includes a marking element 2. The marking element 2 in turn has two marking blades 3, which are equipped with serrated contact surfaces 4.

The marking blades 3 or the marking element 2 is firmly integrated in the marking head 1.

Furthermore, a holding device 5 is provided which carries the marking head 1 or an intermediate adapter. The marking head 1 has a bearing area 6 that is rotatably mounted in a bearing ring 7 of the holding device 5 encompassing the bearing area 6 in an angular position that can be predetermined or changed.

The marking head 1 is rotatably inserted by hand or tool into the body of the bearing area 6 and held there more or less non-rotatably, wherein the entire arrangement, that is, the marking head 1 and the bearing area 6, is arranged rotatably within the bearing ring 7 or extends all the way through it.

The bearing ring 7 is firmly connected with an angled handle part 8 of a hand instrument.

At the end of the marking head 1 that is opposite the marking blades 3 and extends with the bearing area 6 through the bearing ring 7, a pendulum 9 is provided which holds or aligns the marking head 1, which is rotatably mounted in the bearing ring 7, in its position (vertical or horizontal) as given by the pendulum 9. Regardless of how the handle part 8 is held, the pendulum 9 aligns the marking head 1 in the preset angular position.

For setting or checking the preset angular position of the marking head 1, a scale ring 10 is provided as an outer ring on the marking head 1 and is equipped with a scale 18 in the range from 0° to 180°.

The sleeve 11 forming the bearing area 6 has spring-tensioned means holding the marking head 1 inserted there in the respective angular position. A marking ring 12 is non-rotatably connected with the sleeve 11 and has a triangle, an arrow, a line, or the like as a marking that marks the angular position of the scale ring 10.

Advantageously, the pendulum marker according to FIG. 1 can be disassembled into its components or its individual parts exchanged.

Figure 2:
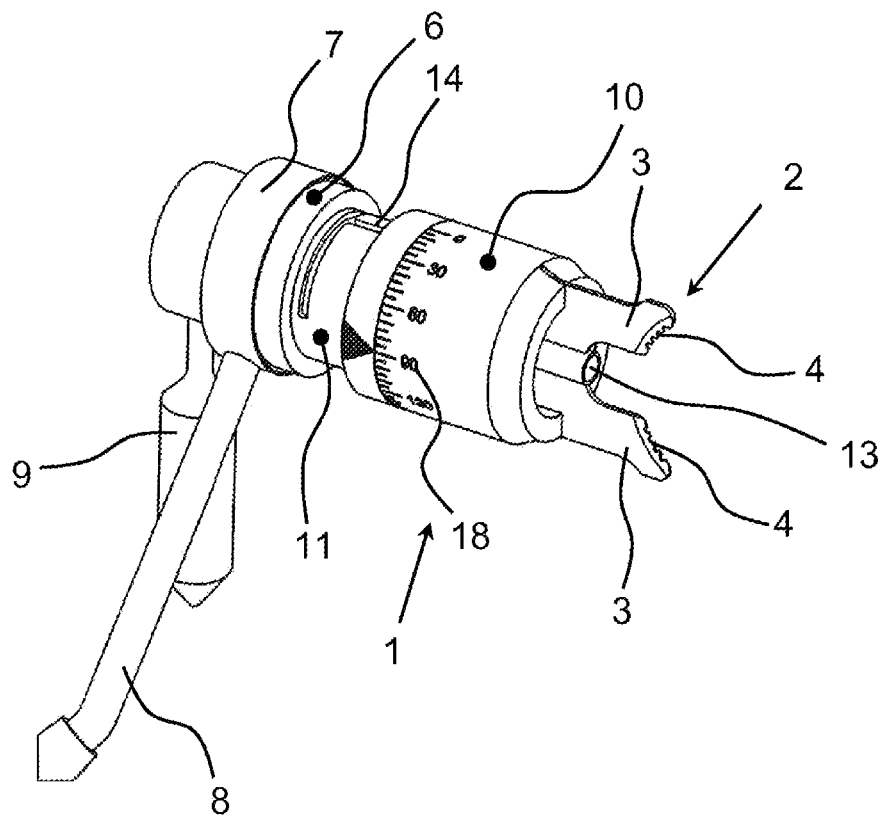
FIG. 2 shows a schematic view, enlarged, of the marking head together with the holding device from FIG. 1.

FIG. 2 shows an enlarged view of the marking head 1 of the pendulum marker from FIG. 1. Here it can clearly be seen that between the two opposing marking blades 3 a sighting tube 13 is arranged which extends at least for a certain distance through the marking head 1. The entire arrangement has a co-axial passage that at the end opposite the marking element 2 is open to permit looking into or through it and in the direction of the marking element 2 opens out into the sighting tube 13. This enables a position on the eye to be targeted before the marking element 2 with its marking blades 3 is placed on the cornea of the eye in order to mark it.

FIG. 2 clearly shows the configuration of the bearing area 6 or of the sleeve 11 carrying the bearing area 6, which is equipped with clamping means 14 for more or less non-rotatably fixing or clamping the marking head 1.

Figure 3:
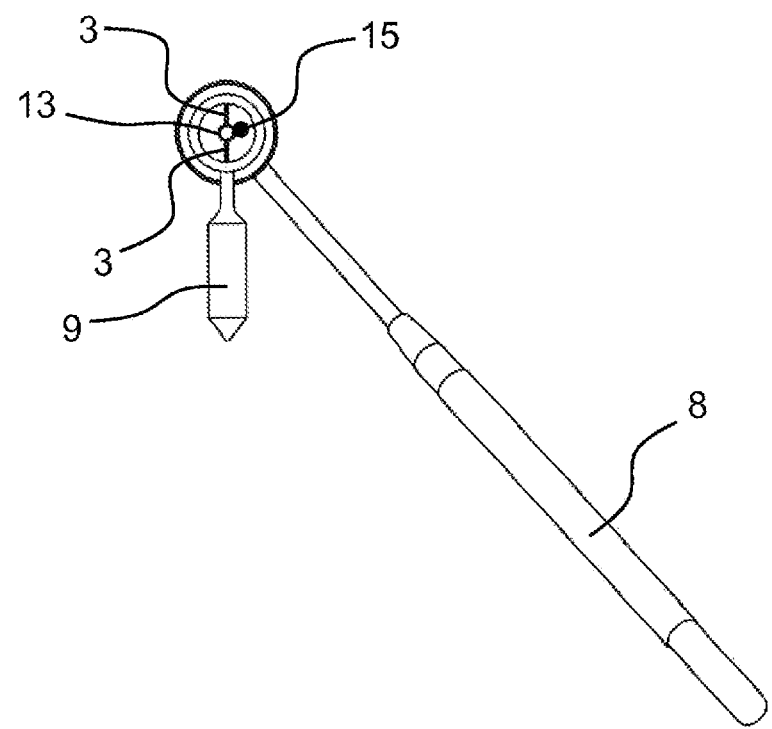
FIG. 3 shows a schematic view, from the rear side, of the device from FIG. 1.

FIG. 3 shows the object from FIG. 1 in a schematic view from the rear side, that is, facing away from the distal end. The coaxial passage 15 and the central sighting tube 13 can be seen. The marking blades 3 are arranged on both sides of the sighting tube 13.

Figure 4:
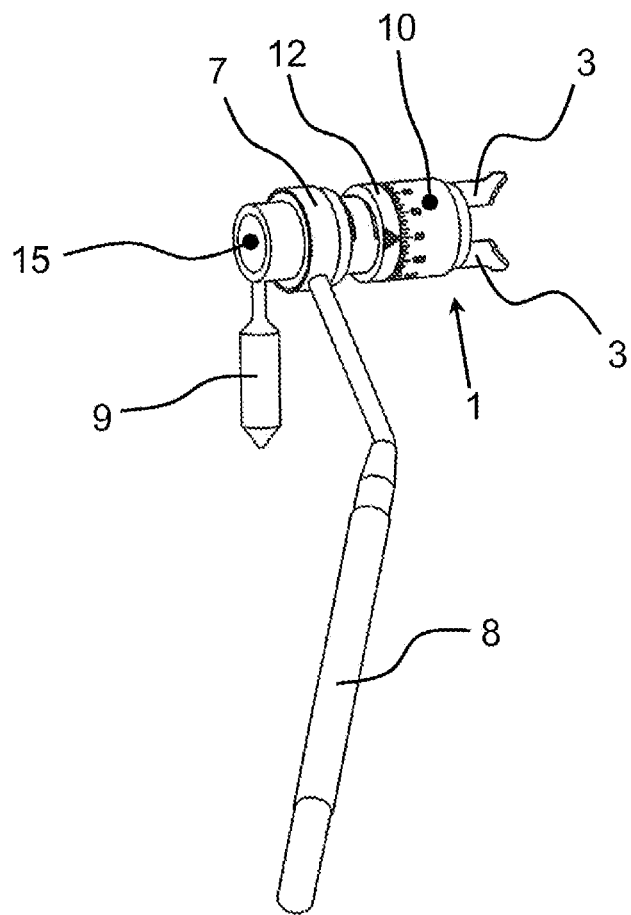
FIG. 4 shows a schematic side view of the device from FIG. 1.

FIG. 4 shows the pendulum marker from FIG. 1 from a different angle. It is easy to see how the marking on the marking ring 12 shows the angular position on the scale ring 10 corresponding to the preset angular position of the marking head 1 or marker element 2 and thus of the marking blades 3.

Figure 5:
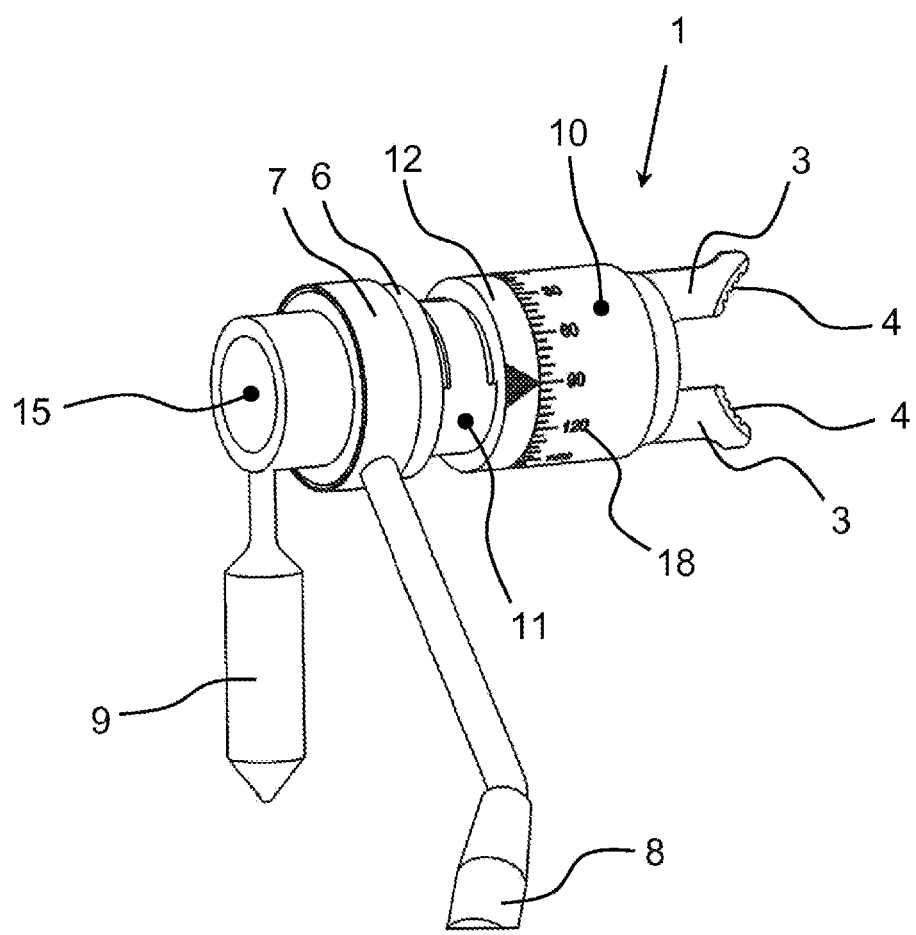
FIG. 5 shows a schematic side view, enlarged, of the device from FIG. 4.

FIG. 5 shows the marking head 1 in an enlarged view corresponding to the preceding explanations.

Figure 6:
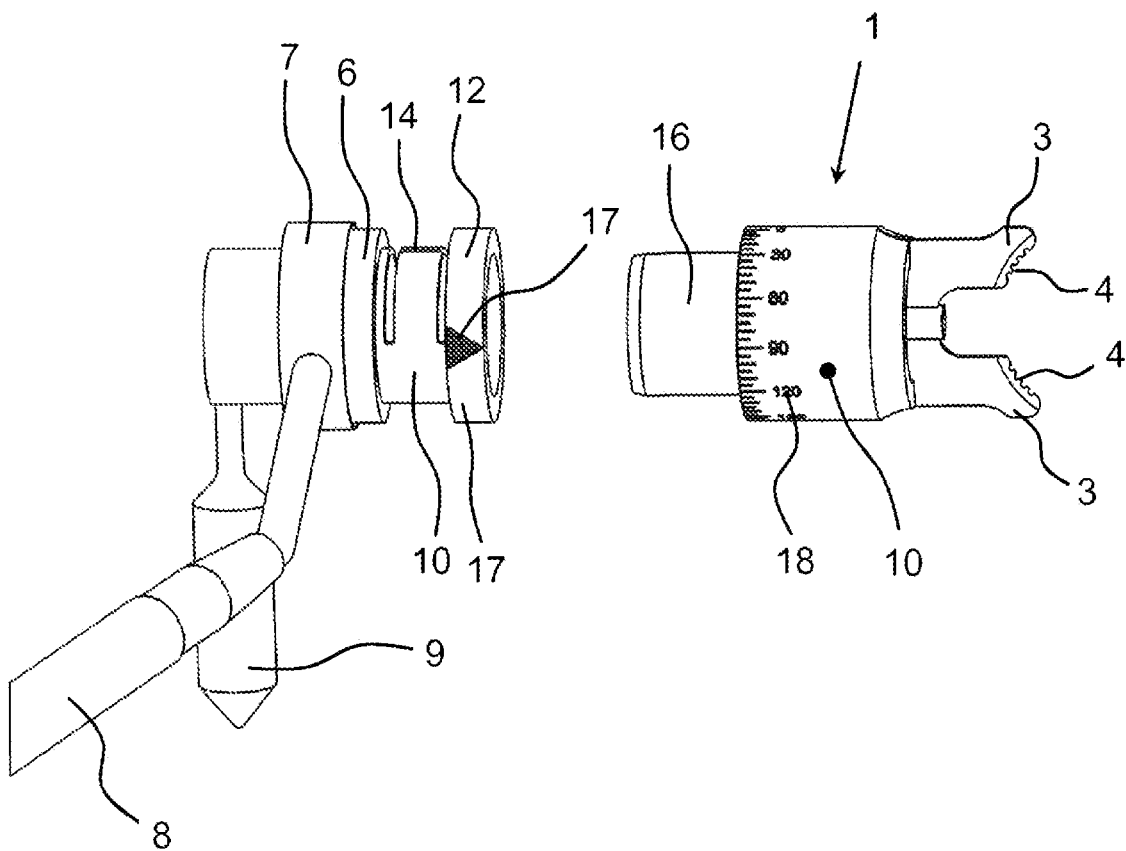
FIG. 6 shows a schematic side view of the device from FIGS. 1 through 5, enlarged, with the marking head pulled out.

FIG. 6 shows the object from FIG. 5, wherein the marking head 1 is equipped with a plug-in sleeve 16 serving for insertion. The latter, overcoming the clamping force of the clamping means 14, can be plugged or pressed through the marking ring 12 into the sleeve 11 that forms the bearing area 6. The angular position of the marking head 1 can be changed by overcoming the clamping force of the clamping means 14, wherein the angular position is shown by the marking 17 on the marking ring 12 and the marking 17 points towards the opposite scale 18 on the scale ring 10.

Figure 7:
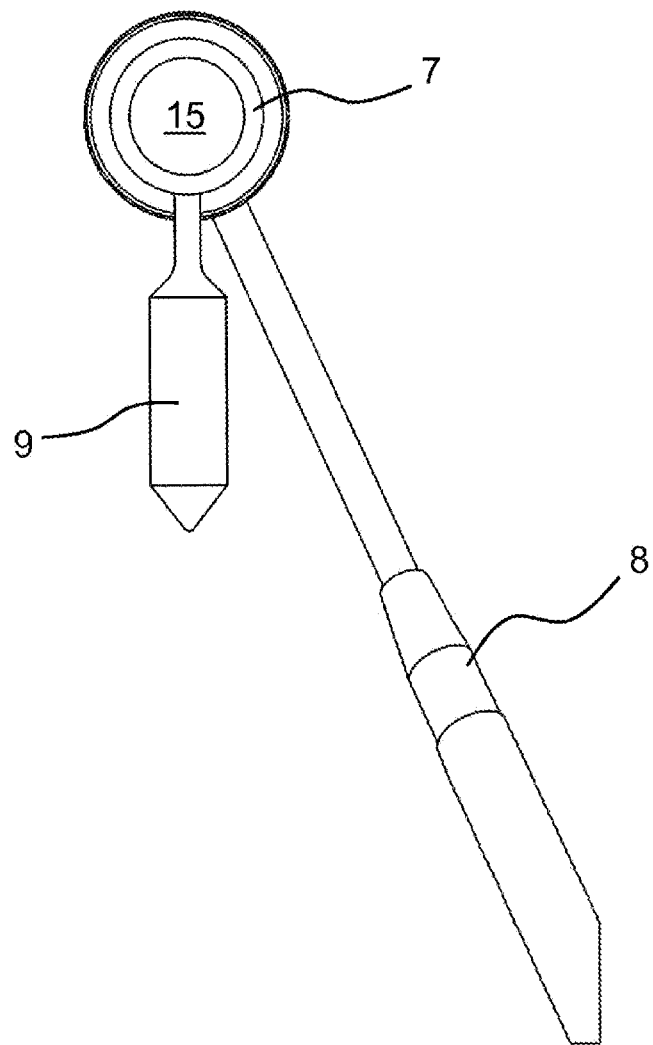
FIG. 7 shows a schematic view of the device from FIGS. 1 through 6, seen from the rear side of the holding device, without the marking head.

FIG. 7 shows the object from FIG. 6 from the rear side, with the marking head absent. The coaxial passage 15 is completely unobstructed.

Figure 8:
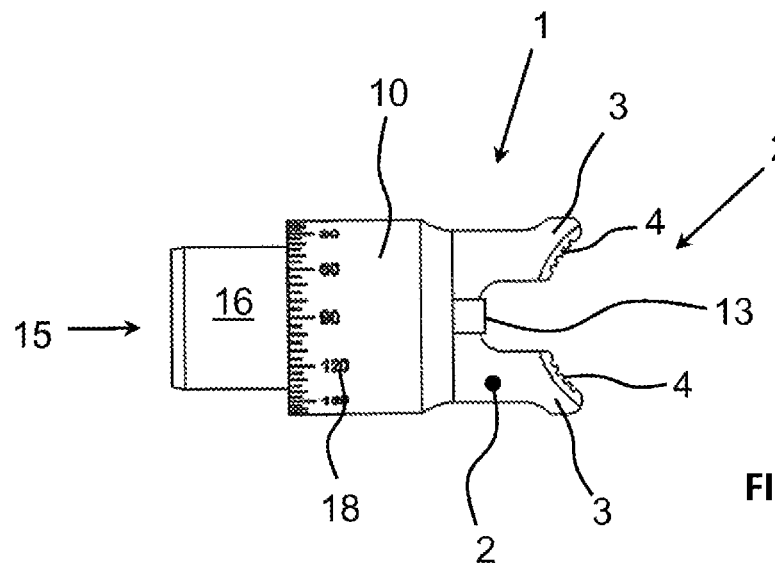
FIG. 8 shows a schematic side view of the marking head of the device from FIGS. 1 through 7.

FIG. 8 shows the marking head 1 on its own with the outer scale ring 10 and also the scale 18. The marking element 2 with the two marking blades 3 is located at the distal end. The sighting tube 13 is arranged centrally.

The plug-in sleeve 16 is located at the end of the marking head 1 opposite the distal end.

Figure 9:
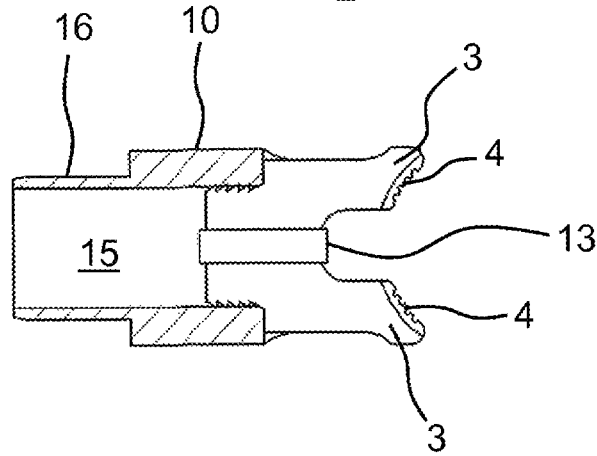
FIG. 9 shows a schematic sectional view of the object from FIG. 8.

FIG. 9 shows a sectional view of the object from FIG. 8. The arrangement and design of the sighting tube 13 can be seen. The outer scale ring 10 is made in one piece with the plug-in sleeve 16.

Figure 10:
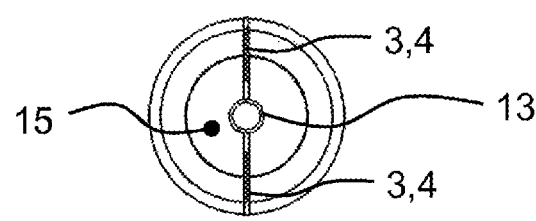
FIG. 10 shows a schematic front view, that is, seen from the marking blades, of the object from FIGS. 8 and 9.

FIG. 10 shows the object from FIGS. 8 and 9 from the distal end, wherein the coaxial sighting tube 13 and the marking blades 3 can be seen together with the serrated contact surfaces 4.

Figure 11:
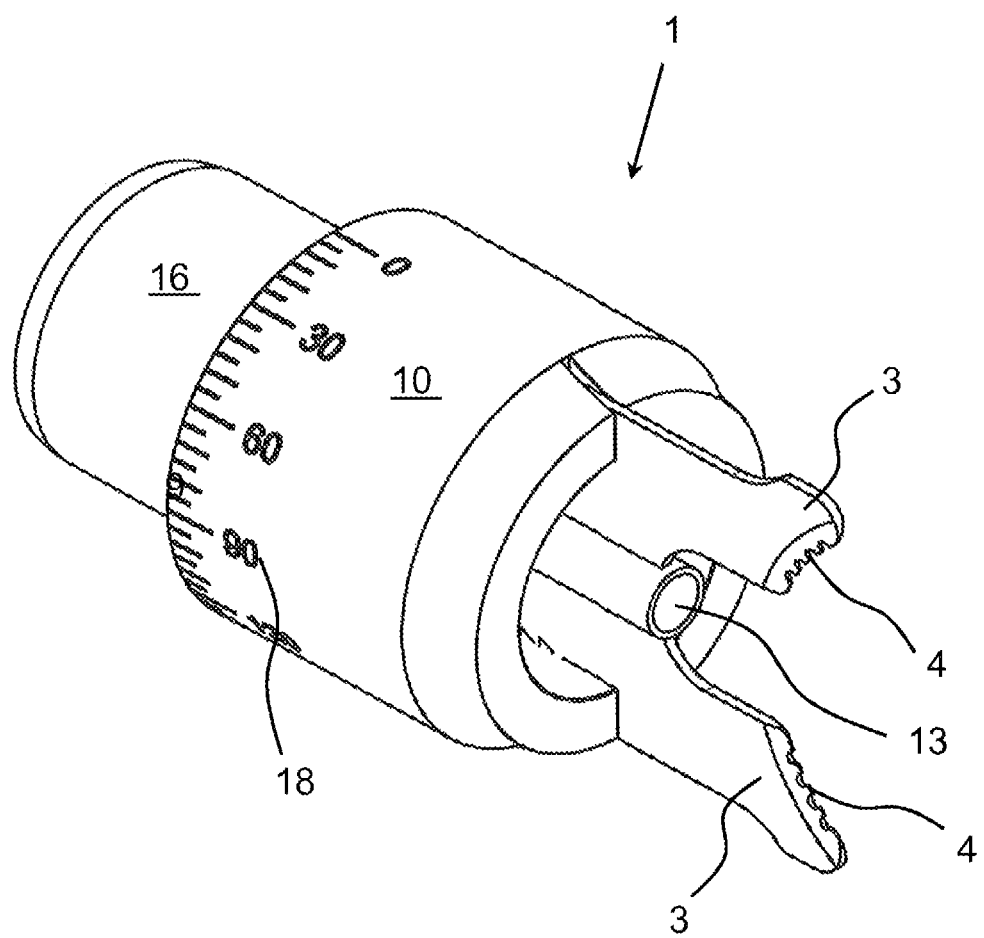
FIG. 11 shows a schematic view, enlarged, of the marking head according to FIGS. 6 and 8.

FIG. 11 shows the marking head 1 in an enlarged view, wherein the arrangement of the sighting tube 13 is particularly easy to identify. The outer scale ring 10 is integrally formed with the plug-in sleeve 16, namely, for non-rotatable insertion into the previously mentioned sleeve 11, which forms the bearing area 6, which is rotatably mounted in the bearing ring 7.

Figure 12:
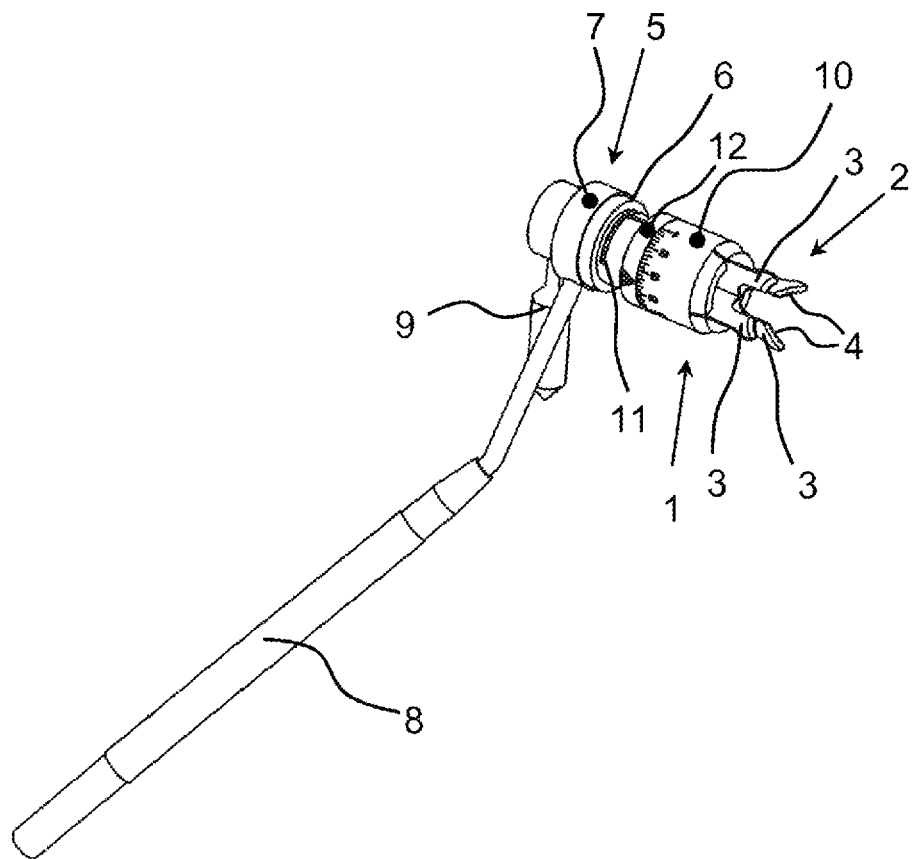
FIG. 12 shows a schematic view of a second exemplary embodiment of a device according to the present disclosure in the form of a so-called pendulum marker, comprising a marking head with a marking element having four marking blades.

FIG. 12 shows a further exemplary embodiment of the pendulum marker from FIGS. 1 through 11, which differs from the exemplary embodiment from FIGS. 1 through 11 in that the marking element 2 has a total of four pairwise-opposing marking blades 3. The central sighting tube according to the exemplary embodiment from FIGS. 1 through 11 is not present there, wherein a rear-side view through the entire arrangement is possible. This exemplary embodiment has otherwise the same features as the exemplary embodiment from FIGS. 1 through 11, so that further detailed explanations are not required.

Figure 13:
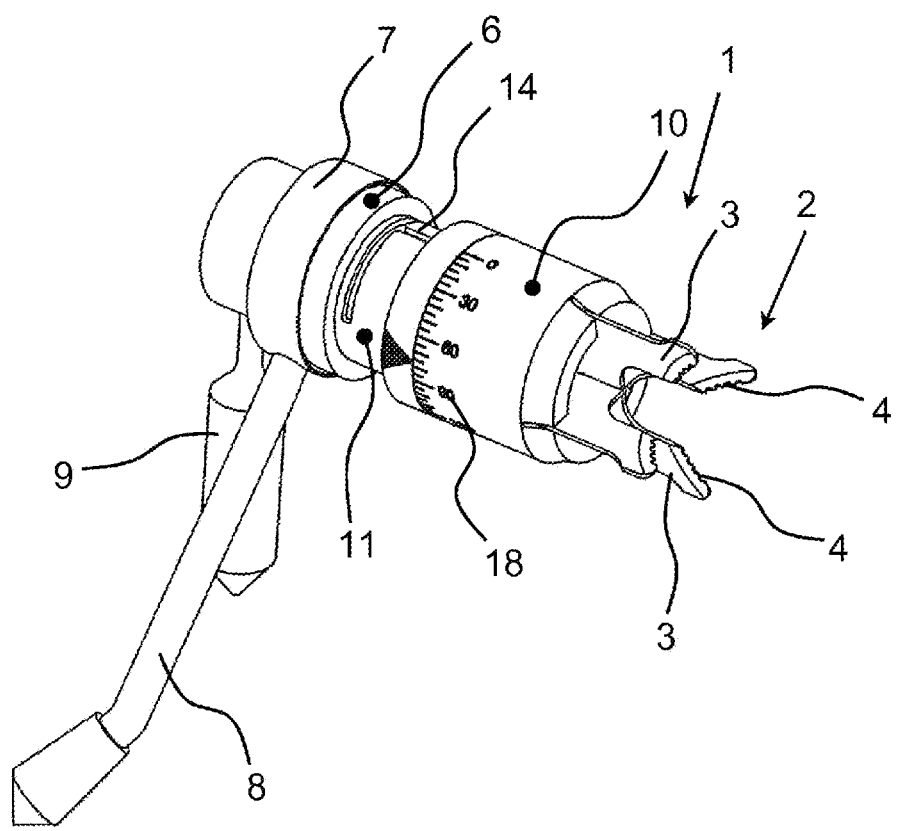
FIG. 13 shows a schematic view, enlarged, of the marking head together with the holding device from FIG. 12.

FIG. 13 shows the exemplary embodiment from FIG. 12 with the marking head 1 enlarged. The marking element 2 with a total of four marking blades 3 is particularly easy to recognize here.

Figure 14:
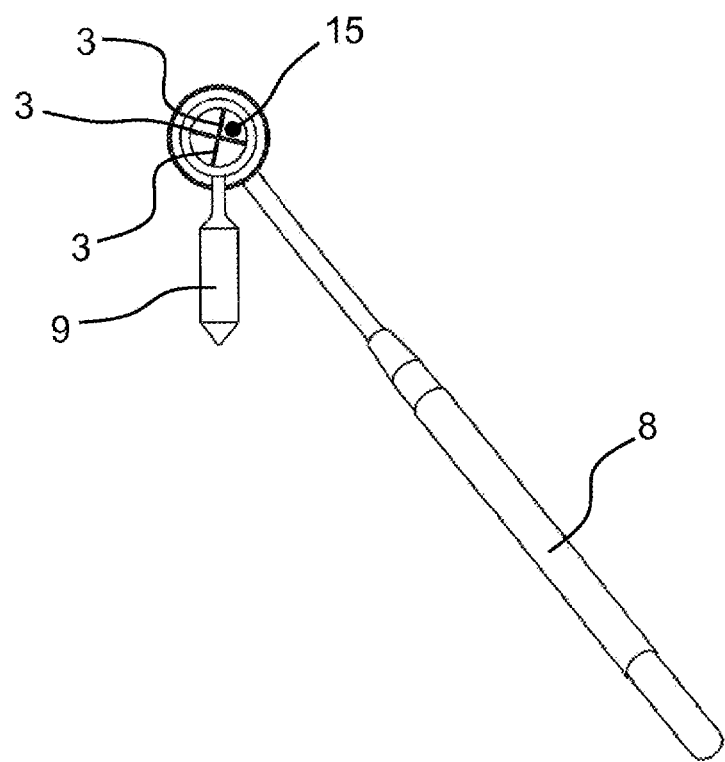
FIG. 14 shows a schematic view, from the rear side, of the device from FIG. 12.

FIG. 14 shows the object from FIGS. 12 and 13 from the rear side, wherein this view enables the coaxial passage 15 to be seen. The marking element 2 with the four marking blades 3 is arranged at the distal end.

Figure 15:
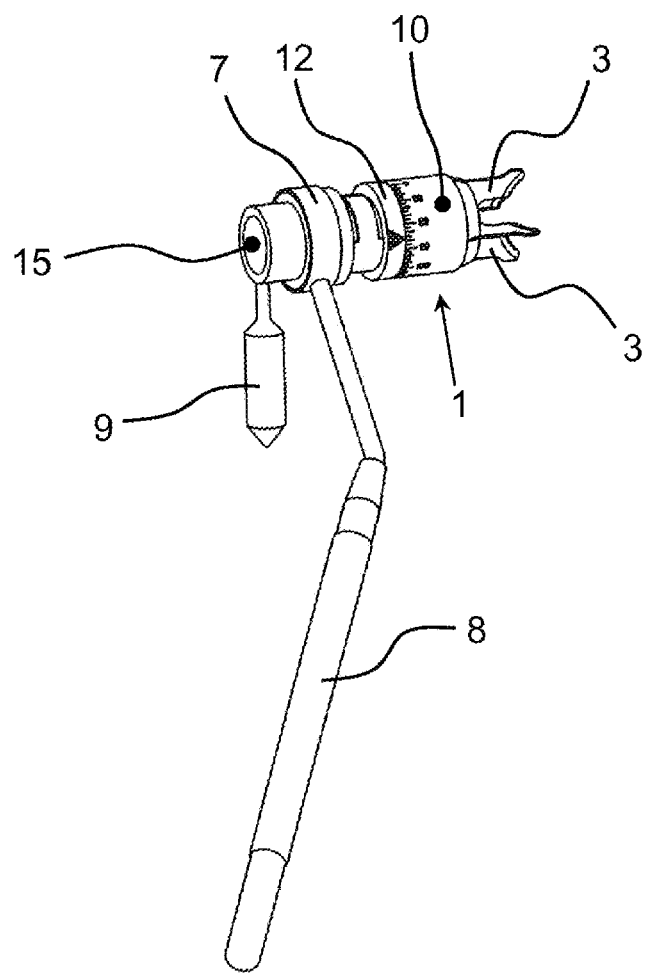
FIG. 15 shows a schematic side view of the device from FIG. 12.

FIG. 15 shows the object from FIGS. 12 to 14 from a different angle, wherein the marking element 2 with the four marking blades 3 can also be seen.

Figure 16:
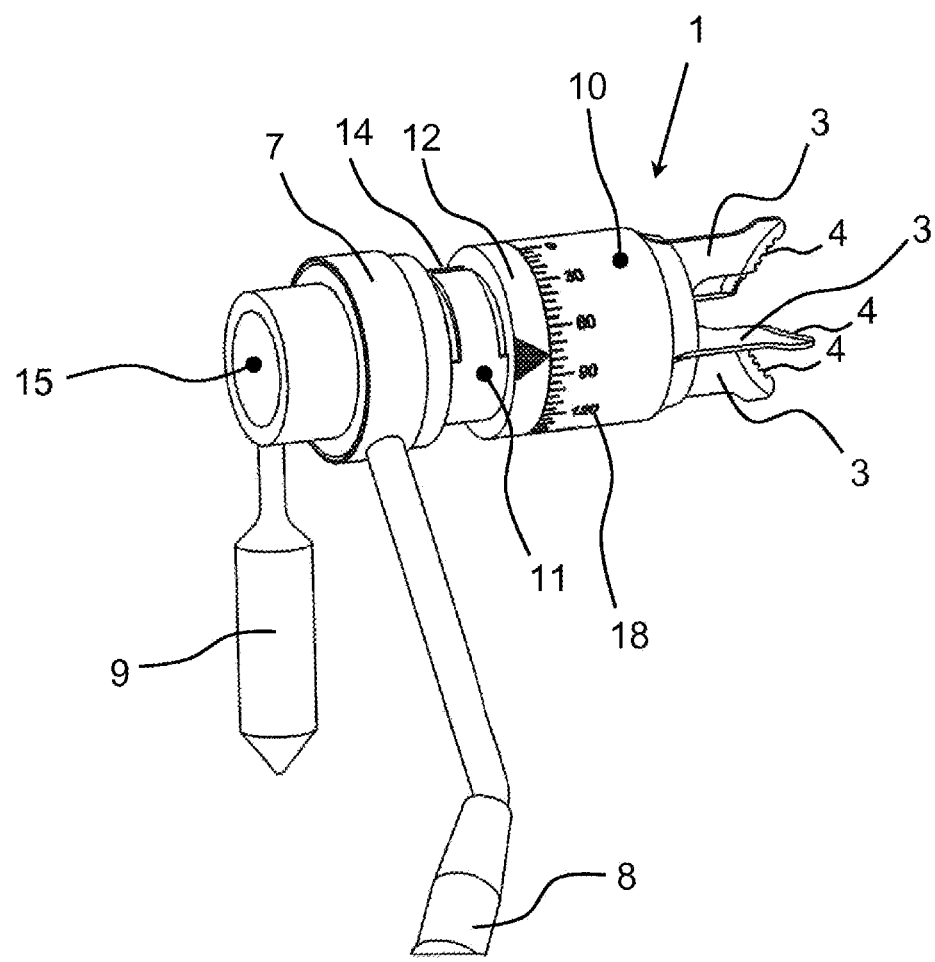
FIG. 16 shows a schematic side view, enlarged, of the device from FIG. 15.

FIG. 16 shows the object from FIG. 15 in an enlarged view, wherein the marking element 2 with the four marking blades 3 appears in detail.

Figure 17:
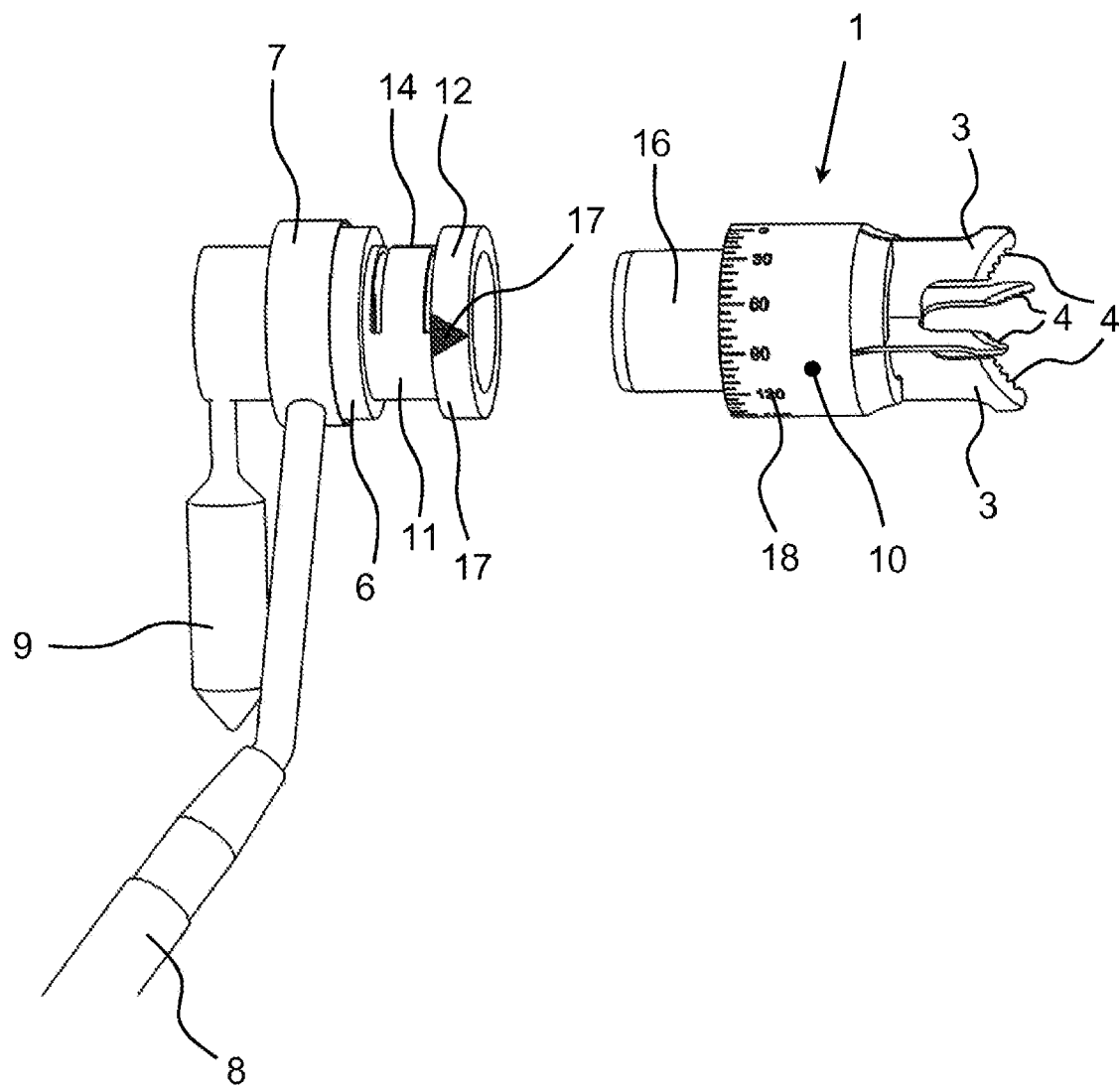
FIG. 17 shows a schematic side view of the device from FIGS. 12 through 16, enlarged, with the marking head pulled out.

FIG. 17 shows the exemplary embodiment from FIGS. 12 through 16 with the marking head 1 pulled out. Clearly visible is the plug-in sleeve 16 which can be inserted right through the marking ring 12 and into the sleeve 11 of the bearing area 6 while overcoming the clamping force of clamping means 14 and which can be fixed in an angular position. Regarding setting and reading off the angular position, to avoid repetition refer to the comments on the first exemplary embodiment.

Figure 18:
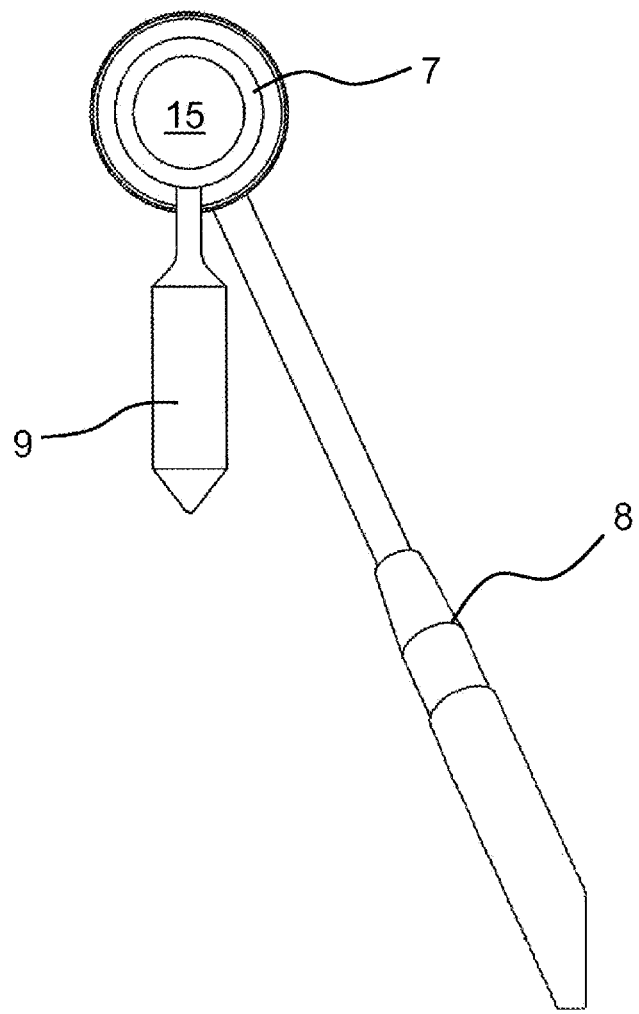
FIG. 18 shows a schematic view of the device from FIGS. 12 through 17 seen from the rear side of the holding device, without the marking head.

FIG. 18 shows the object from FIG. 17 without the marking head. The coaxial passage 15 is unobstructed.

Figure 19:
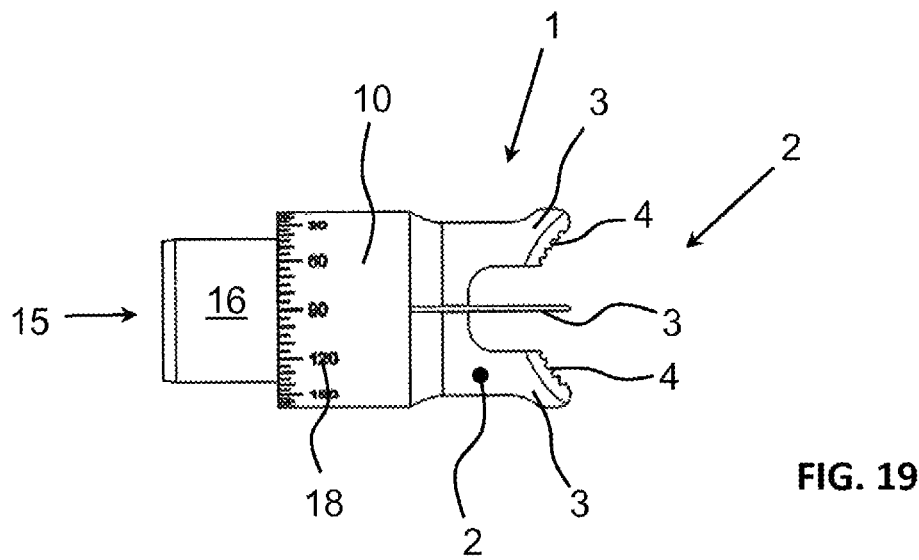
FIG. 19 shows a schematic side view of the marking head of the device from FIGS. 12 through 18.

FIG. 19 shows the marking head 1 of the exemplary embodiment from FIGS. 12 to 18 with a marking element 2 that comprises a total of four marking blades 3.

Figure 20:
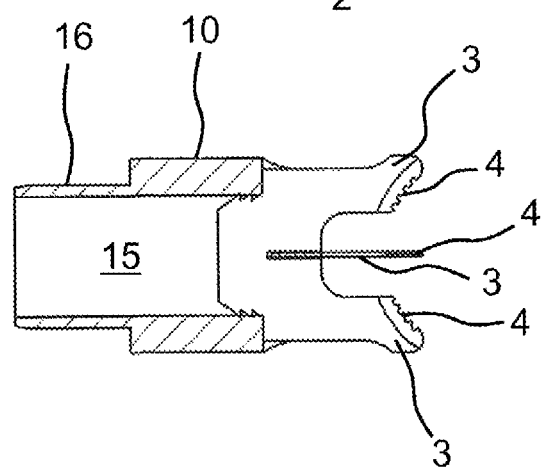
FIG. 20 shows a schematic sectional view of the object from FIG. 19.

FIG. 20 shows a sectional view of the object from FIG. 19. Here, too, the four marking blades 3 are clearly visible. The scale ring 10 and the plug-in sleeve 16 are integral components of the marking head 1.

Figure 21:
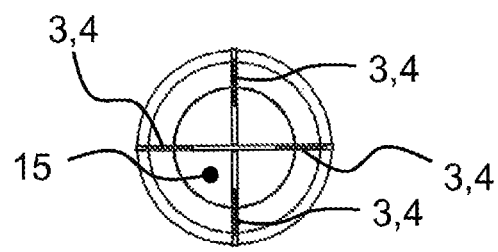
FIG. 21 shows a schematic front view, that is, seen from the marking blades, of the object from FIGS. 19 and 20.

FIG. 21 shows the object from FIGS. 19 and 20 from the distal end, namely the marking head 1. It can be clearly seen that the marking element 2 comprises a total of four marking blades 3.

Figure 22:
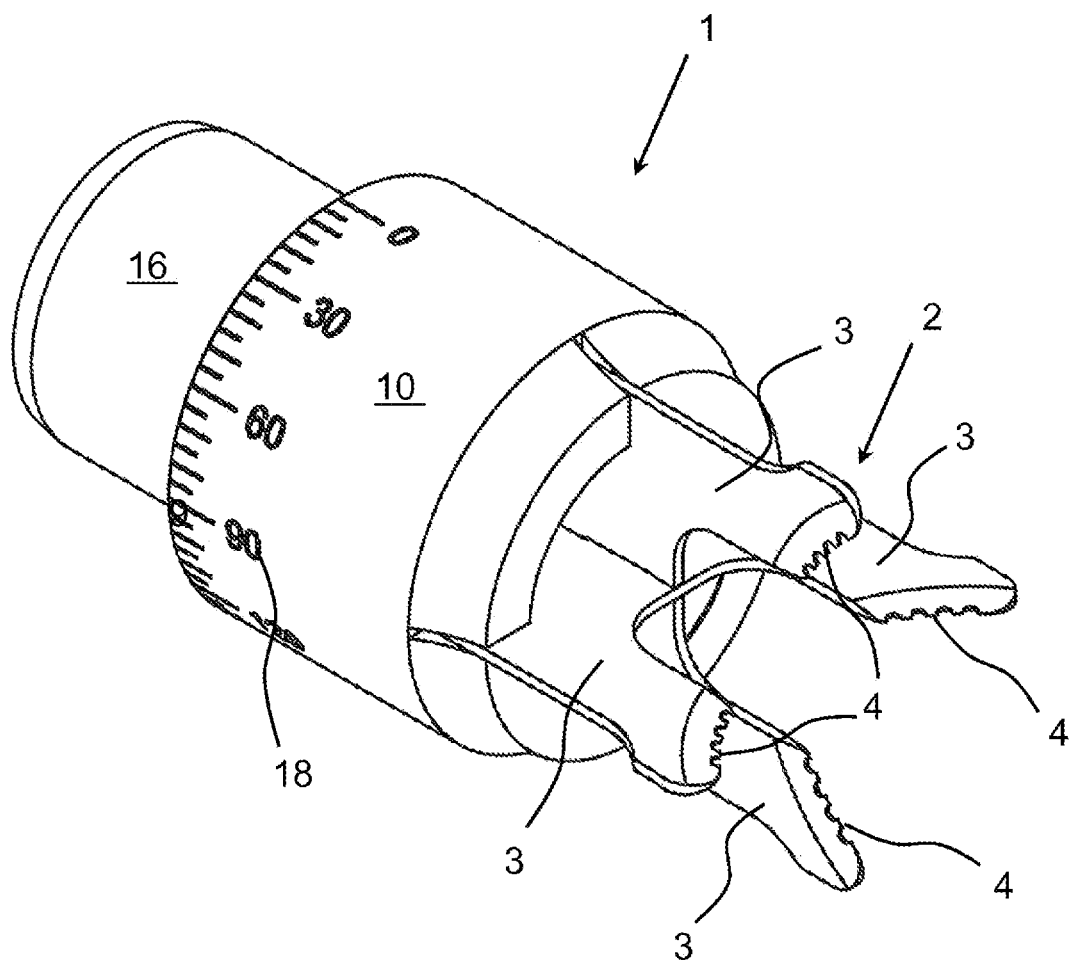
FIG. 22 shows a schematic view, enlarged, of the marking head according to FIGS. 17 and 19.

Finally, FIG. 22 shows the marking head 1 of the exemplary embodiment from FIGS. 1 to 21 in an enlarged view. The marking element 2 has four marking blades 3, each at the distal end, having contact surfaces 4 that are serrated. The term "contact surface" is to be understood in the broadest sense. It can also be a contact line or, due to the serrated design, contact points.

With regard to other advantageous embodiments of the device according to the present disclosure, to avoid repetition, refer to the general part of the description and also to the accompanying claims.

Finally, it should be expressly pointed out that the above-described exemplary embodiments of the device according to the present disclosure serve only to explain the claimed teaching, but they are not restricted to the exemplary embodiments.

LIST OF REFERENCE SYMBOLS

1 Marking head
2 Marking element
3 Marking blade
4 Contact surface, contact line, contact point (of the marking blade)
5 Holding device
6 Bearing area
7 Bearing ring
8 Handle part
9 Pendulum, weight
10 Scale ring
11 Sleeve (forms the bearing area)
12 Marking ring
13 Sighting tube
14 Clamping means
15 Coaxial passage
16 Plug-in sleeve
17 Marking (on the marking ring)
18 Scale The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device for applying a marking to the cornea of a human eye, the device having a marking head and a holding device,
    wherein the marking head comprises a marking element,
    wherein the holding device comprises a bearing ring that is non-rotatably connected to a handle part that, in use, is grasped by a hand of an operator of the device, the bearing ring being configured to rotatably carry the marking head or an intermediate adapter such that the marking head or the intermediate adapter rotates and is oriented using gravity separate from an orientation of the handle part,
    wherein the marking head or the intermediate adapter includes a bearing area having a body,
    wherein the marking head comprising the marking element is rotatably inserted into the body of the bearing area to set the marking element in an angular position with respect to the bearing area and thereafter, in use, held there non-rotatably,
    wherein the bearing ring of the holding device encompasses the bearing area of the marking head or the intermediate adapter, and
    wherein the bearing area, which is set in the angular position with respect to the marking element, is rotatably mounted in the bearing ring of the holding device, wherein the angular position can be predetermined or changed.

2. The device according to claim 1, wherein a ball bearing is provided for mounting the bearing area of the marking head or the intermediate adapter in the bearing ring of the holding device or vice versa.

3. The device according to claim 2, wherein the ball bearing is made of stainless steel and/or ceramic.

4. The device according to claim 1, wherein the marking head and, if applicable, the intermediate adapter has a passage that, in a region of the marking element, terminates with a coaxial sighting tube.

5. The device according to claim 4, wherein the passage is a coaxial passage.

6. The device according to claim 1, wherein the marking element comprises two or four marking blades lying opposite to each other in pairs.

7. The device according to claim 6, wherein the marking blades are designed for marking a straight line or at least two points or sections of a straight line.

8. The device according to claim 6, wherein the marking blades are serrated.

9. The device according to claim 8, wherein the marking blades are at least partially curved to conform to an ocular surface of the eye.

10. The device according to claim 1, wherein the marking head can be set or adjusted in its angular position by hand or by way of a tool.

11. The device according to claim 1, wherein a marking ring of the of the marking head has a marking symbolizing the angular position and a scale ring of the marking head has a scale for indicating the angular position.

12. The device according to claim 11, wherein the scale for indicating the angular position is in the range of 0° to 180°.

13. The device according to claim 1, further comprising coupling means acting between the marking head and the holding device or the intermediate adapter.

14. The device according to claim 13, wherein the coupling means comprise a spring-tensioned means for mutual fixing or latching.

15. The device according to claim 1, wherein a conventional ophthalmological device serves as the holding device.

16. The device according to claim 15, wherein the conventional ophthalmological device serving as the holding device is a slit lamp.

17. The device according to claim 15, wherein the marking head is connected to the device via a coupling means or an adapter comprising a connector.

18. The device according to claim 1, wherein a hand-held ophthalmological instrument serves as the holding device.

19. The device according to claim 18, wherein the hand-held ophthalmological instrument serving as the holding device has a gravity-loaded pendulum receptacle for the marking head that is aligned in a horizontal or vertical direction.

20. The device according to claim 1, wherein the bearing ring is non-removably connected to the handle part.

* * * * *